(12) United States Patent
Chauvin et al.

(10) Patent No.: US 11,161,810 B1
(45) Date of Patent: Nov. 2, 2021

(54) CONTINUOUS PHOTOCHEMICAL PRODUCTION OF HIGH PURITY LINEAR MERCAPTAN AND SULFIDE COMPOSITIONS

(71) Applicant: Arkema Inc., King of Prussia, PA (US)

(72) Inventors: Jean-Philippe R. Chauvin, King of Prussia, PA (US); Brian E. Lordan, Phoenixville, PA (US); Patricia Wing-Kee Cheung, West Chester, PA (US); Vijay R. Srinivas, Exton, PA (US); Andrew D. Polli, Washington Crossing, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 16/897,387

(22) Filed: Jun. 10, 2020

(51) Int. Cl.
| | |
|---|---|
| *C07C 319/04* | (2006.01) |
| *B01J 19/12* | (2006.01) |
| *C07C 319/28* | (2006.01) |
| *B01D 3/06* | (2006.01) |

(52) U.S. Cl.
CPC .......... *C07C 319/04* (2013.01); *B01J 19/123* (2013.01); *C07C 319/28* (2013.01); *B01D 3/06* (2013.01); *B01J 2219/00101* (2013.01)

(58) Field of Classification Search
CPC .... C07C 319/04; C07C 319/28; B01J 19/123; B01J 2219/00; B01D 3/06
See application file for complete search history.

(56) References Cited

U.S. PATENT DOCUMENTS

| | | | | |
|---|---|---|---|---|
| 2,398,479 | A * | 4/1946 | Vaughan | C07C 319/04 204/157.76 |
| 2,427,309 | A * | 9/1947 | Schulze | C07C 319/04 568/72 |
| 4,927,972 | A * | 5/1990 | Arretz | C07C 319/06 554/101 |
| 2017/0334843 | A1 * | 11/2017 | Kreider | C07C 319/16 |

FOREIGN PATENT DOCUMENTS

WO  WO-2017127508 A1 * 7/2017 ............... B01D 3/42

* cited by examiner

*Primary Examiner* — Rosalynd A Keys
(74) *Attorney, Agent, or Firm* — Steven D. Boyd

(57) ABSTRACT

Continuous photochemical production of high purity linear mercaptan and sulfide-containing compositions.

24 Claims, 6 Drawing Sheets

CONTINUOUS PHOTOCHEMICAL PRODUCTION OF HIGH PURITY LINEAR MERCAPTAN AND SULFIDE COMPOSITIONS

FIELD OF THE INVENTION

The present invention relates to the continuous photochemical production of high purity linear mercaptan and sulfide-containing compositions.

BACKGROUND

Mercaptans find utility in such wide-ranging technical areas as biocorrosion inhibitors, anti-fungal drugs, chain-transfer agents in polymerizations, coating agents for metallic surfaces and vulcanization accelerators for rubber. Sulfides are key intermediates in organic synthesis and are important components of many fine chemicals such as perfumes and cosmetics. In several of these applications, it is critical that the mercaptan or sulfide is of high purity.

There is always a need for improved large-scale preparations of high-purity mercaptans and sulfides, especially without relying on the presence of various reaction promoters or photoinitiators.

SUMMARY

The present invention achieves these objectives of providing high purity mercaptans and sulfides as described herein.

In particular, the invention provides a process for producing a high purity product thiol from hydrogen sulfide and an olefin. The process for producing the high purity thiol includes the following steps. Feeding the hydrogen sulfide and the olefin to a reactor system. The reactor system is configured to form a reactor effluent stream including the product thiol, unreacted hydrogen sulfide, unreacted olefin and other components. Recycling a first portion of the reactor effluent stream to the reactor system. Feeding a second portion of the reactor effluent stream to a flash vaporizer. The flash vaporizer is configured to produce a hydrogen sulfide recycle stream including at least a portion of the unreacted hydrogen sulfide, and a crude thiol stream including the product thiol, the unreacted olefin and the other components. Feeding the hydrogen sulfide recycle stream to the reactor system. Feeding the crude thiol stream to a crude thiol separation system. The crude thiol separation system is configured to separate at least a portion of the unreacted olefin from the crude thiol stream. The separation step produces an olefin recycle stream including the unreacted olefin, a first by-product stream including a first portion of the other components, and a crude thiol product stream including the product thiol and a second portion of the other components. Feeding the olefin recycle stream back to the reactor system. Feeding the crude thiol product stream to a product thiol purification unit. The product thiol purification unit is configured to produce a thiol product stream comprising purified product thiol comprising at least 90 weight percent of the product thiol and a second by-product stream comprising the second portion of the other components.

An apparatus for producing a high purity product thiol from hydrogen sulfide and an olefin is provided. The apparatus includes a reactor system configured to receive the hydrogen sulfide and the olefin and to produce a reactor effluent stream. The reactor effluent stream includes the product thiol, unreacted hydrogen sulfide, unreacted olefin and other components. The reactor system is further configured to recycle a first portion of the reactor effluent stream back the reactor system. The apparatus also includes a flash vaporizer in communication with the reactor system. The flash vaporizer is configured to receive a second portion of the reactor effluent stream and to produce a hydrogen sulfide recycle stream that includes at least a portion of the unreacted hydrogen sulfide. The flash vaporizer also produces a crude thiol stream including the product thiol, the unreacted olefin and the other components. The flash vaporizer is configured to feed the hydrogen sulfide recycle stream back to the reactor system. The apparatus for producing the purified thiol also includes a crude thiol separation system in communication with the flash vaporizer and the reactor system. The crude thiol separation system is configured to receive the crude thiol stream. The crude thiol separation system is configured to separate at least a portion of the unreacted olefin from the crude thiol stream to produce an olefin recycle stream including the unreacted olefin, a first by-product stream including a first portion of the other components, and a crude thiol product stream including the product thiol and a second portion of the other components. The crude thiol separation system also is configured to feed the olefin recycle stream to the reactor system. The apparatus for producing the purified thiol also includes a product thiol purification unit in communication with the crude thiol separation system. The product thiol purification unit is configured to receive the crude thiol product stream and to produce a product thiol stream comprising purified product thiol and a second by-product stream comprising the second portion of the other components. The purified product thiol stream includes at least 98.5 weight percent of the product thiol.

A process for producing a high purity product sulfide from hydrogen sulfide or $R^1SH$, and an olefin of formula $C_xH_{(2x)}$ is provided. The process for producing the high purity product sulfide includes the following steps. Feeding the hydrogen sulfide or the $R^1SH$, and the olefin of formula $C_xH_{(2x)}$ to a reactor system. The reactor system is configured to form a reactor effluent stream including the product sulfide, unreacted hydrogen sulfide or unreacted olefin of formula $C_xH_{(2x)}$, unreacted $R^1SH$, and other components. Recycling a first portion of the reactor effluent stream to the reactor system. Feeding a second portion of the reactor effluent stream to a sulfide separation system. The sulfide separation system is configured to produce at least one recycle stream comprising at least a portion of the unreacted hydrogen sulfide, the unreacted olefin of formula $C_xH_{(2x)}$, the unreacted $R^1SH$, and other components, as well a product stream including the high purity product sulfide.

An apparatus for producing a high purity product sulfide from hydrogen sulfide or $R^1SH$, and an olefin of formula $C_xH_{(2x)}$ is provided. The apparatus for producing the high purity sulfide includes a reactor system. The reactor system is configured to receive the hydrogen sulfide or the $R^1SH$, and the olefin of formula $C_xH_{(2x)}$ and to form a reactor effluent stream. The reactor effluent stream includes the product sulfide, unreacted hydrogen sulfide or unreacted olefin of formula $C_xH_{(2x)}$, unreacted $R^1SH$, and other components. The reactor system is also configured to recycle a first portion of the reactor effluent stream back to the reactor system. The apparatus to produce the purified sulfide also includes a sulfide separation system in communication with the reactor system. The sulfide separation system is configured to and is configured to receive a second portion of the reactor effluent stream from the reactor system as well as to produce at least one recycle stream including at least a portion of the unreacted hydrogen sulfide, the unreacted olefin of formula $C_xH_{(2x)}$, the unreacted $R^1SH$, and other components, and a product stream comprising the high purity product sulfide.

BRIEF DESCRIPTION OF THE DRAWINGS

The following figures are merely illustrative of various specific embodiments of the present invention and are not intended to otherwise limit the scope of the invention as described herein.

FIG. 5 shows an exemplary process to produce a high purity sulfide according to an embodiment of the invention; and.

FIG. 1 shows a first embodiment of a process to produce a high purity primary thiol. As shown in FIG. 1, hydrogen sulfide and an alpha olefin are fed to a reaction system. The olefin is preferably a linear alpha C4-C18 olefin, i.e., the double bond is terminal on a linear hydrocarbon, preferably n-dodec-1-ene. The reaction system may include an absorber and at least one reactor. The absorber is configured to dissolve the gaseous hydrogen sulfide in the liquid olefin and then to feed the hydrogen sulfide dissolved in the olefin into the reactor, or back or reactors as shown in FIG. 1. The reactor system is configured to form a reactor effluent stream comprising the product thiol, unreacted hydrogen sulfide, unreacted olefin and other components. Non-limiting examples of the other components are secondary thiols, unreacted olefin, and impurities from the incoming olefin feed stream, as well as sulfides. Impurities may include, for example, branched primary thiols (vinylidene mercaptans, 2-ethyl 1-decyl mercaptan, 2-butyl 1-octyl mercaptan), sulfides (e.g., $(C_{12}H_{25})S(C_{12}H_{25})$, $(C_8H_{17})S(C_8H_{17})$); disulfides (e.g., $(C_{12}H_{25})SS(C_{12}H_{25})$, $(C_8H_{17})SS(C_8H_{17})$), secondary thiols (e.g., 2-octanethiol, 2-dodecanethiol), saturated hydrocarbons or paraffins (e.g., octane, decane, dodecane, tetradecane) and internal olefins.

A portion of the reactor effluent stream is immediately recycled back to the reactor system. In an embodiment, the reactor recycle stream is fed back to the absorber, via a recirculating tank that is in communication with the absorber. The remaining portion of the reactor effluent is then fed to a flash evaporator. The flash evaporator is configured to flash off hydrogen sulfide from the reactor effluent to produce a hydrogen sulfide recycle stream and a crude thiol stream. The hydrogen sulfide recycle stream is recycled back to the reactor system. In an embodiment, the hydrogen sulfide recycle stream is fed to the absorber to be dissolved into the olefin. The crude thiol stream is then fed to a crude thiol separation system. As shown in FIG. 1, the crude separation system may include a series of separation units, which are the olefin separation unit and the secondary separation unit in FIG. 1. These separation units are distillation columns, also called "towers", as labelled in FIG. 1. The olefin separation unit is configured to produce an olefin recycle stream as overhead from the column and a secondary stream out the bottom. The secondary stream may include the secondary thiols, i.e., the undesirable thiol components, wherein the —SH group is not in the terminal position on the hydrocarbon group. The olefin recycle stream includes unreacted olefin and is fed back to the reactor system. As shown in FIG. 1, a purge stream may be taken off the olefin recycle stream. The purge stream is intended to remove inerts and undesired heavy olefins, for example. The secondary stream is fed to the secondary separation unit. The secondary stream in this embodiment comprises the desired product thiol as well as secondary thiols, i.e., the —SH group is not terminal. The secondary separation unit is configured to separate the secondary stream to produce a first by-product stream as overhead, which includes the undesired secondary thiols and to also produce a crude thiol product stream as bottoms. This crude product thiol stream is fed to a product thiol purification unit. The product thiol purification unit is a distillation column (labelled "product tower" in FIG. 1) and is configured to produce a thiol product stream as overhead, which is the purified product thiol. The product thiol purification unit also produces a second by-product stream as bottoms that contains other by-product components such as sulfides. This second by-product stream may be fed to a sulfide cracking and stripping unit. The sulfide cracking and stripping unit is configured to recover any thiol in the second by-product stream, convert at least a portion of the sulfides into olefins and thiols and also to produce a third by-product stream comprising any remaining sulfides and other impurities. Sulfhydrolysis of sulfides to mercaptans (thiols) and olefins is well known and can be effected by an acid catalyst (e.g., zeolites) at high temperatures. Complete details can be found in U.S. Pat. Nos. 4,313,006 and 4,396,778, incorporated by reference herein in their entireties for all purposes. The olefins and thiols thus recovered are then fed back to the crude thiol separation system.

FIG. 2 shows the same process as depicted in FIG. 1, but the sulfide cracking and stripping unit is not utilized in this embodiment.

FIG. 3 shows another exemplary embodiment of the process to produce high purity thiol. In this embodiment, the reactor system and the product thiol purification system are the same as shown in FIG. 1. However, the crude thiol separation system has a different arrangement than shown in FIG. 1. In this embodiment, the crude thiol separation system includes an olefin separation unit and a crude thiol separation unit. These two separation units are distillation columns (also called towers in FIG. 3) in this embodiment. As shown in this embodiment, the crude thiol stream emerging from the flash vaporizer is fed to the crude thiol separation unit. The crude thiol separation unit is configured to produce the crude thiol product stream out the bottom and an olefin and a first by-product stream out the top as overhead. The overhead olefin and first by-product stream emerging from the crude thiol separation unit is fed to the bottom of the olefin separation unit. The olefin separation unit is configured to separate the olefin stream to produce a by-product stream as bottoms and the olefin recycle stream as overhead. The olefin recycle stream is fed back to the reactor system. As shown in this embodiment, the crude thiol product stream emerging from the bottom of the crude thiol separation unit is fed to the bottom of the product thiol purification unit (a distillation column, also called a "tower"

in FIG. 3), which is the same arrangement as in FIG. 1. The product thiol purification unit is configured to separate the pure product thiol as the overhead and a second by-product in the bottoms. In this embodiment the sulfide cracking and stripping unit to further separate the bottoms out of the product purification unit is not used, but could be utilized in another embodiment.

FIG. 4 shows a similar embodiment to that shown in FIG. 3, but in this embodiment, the sulfide cracking and stripping unit as described in the embodiment of FIG. 1 is utilized.

FIG. 5 shows an exemplary embodiment of a process for producing a high purity product sulfide from either hydrogen sulfide or thiol having structure $R^1SH$, together with an olefin of formula $C_xH_{(2x)}$ where x is an integer from 2 to 18. As can be seen in FIG. 5, this embodiment process is analogous to the processes of FIGS. 1-4, except that rather than producing a thiol as the desired product and removing unwanted sulfide as an impurity or by-product, the reactor system is operated using conditions that will produce a sulfide as the desired product and the thiol produced in the reactor system as a side product is removed or recycled for further reaction to produce the desired sulfide. If hydrogen sulfide is fed to the reactor system with the olefin of formula $C_xH_{(2x)}$, a sulfide having the structure $S(C_xH_{(2x+1)})_2$ is produced, while if the $R^1SH$ is fed the reactor system with the olefin of formula $C_xH_{(2x)}$, a $S(C_xH_{(2x+1)})(R^1)$ sulfide is produced. As shown in the embodiment of FIG. 5, the hydrogen sulfide or the $R^1SH$, are fed to the reactor system along with the olefin of formula $C_xH_{(2x)}$. As in the previous embodiments, the reactor system may include an absorber and at least one reactor, or a plurality of reactors, called a reactor bank. The absorber, as described in the other embodiments disclosed herein is configured to dissolve the gaseous hydrogen sulfide or liquid $R^1SH$ in the liquid olefin of formula $C_xH_{(2x)}$ and then to feed the hydrogen sulfide or $R^1SH$ dissolved in the olefin of formula $C_xH_{(2x)}$ into the reactor.

Figure 5:
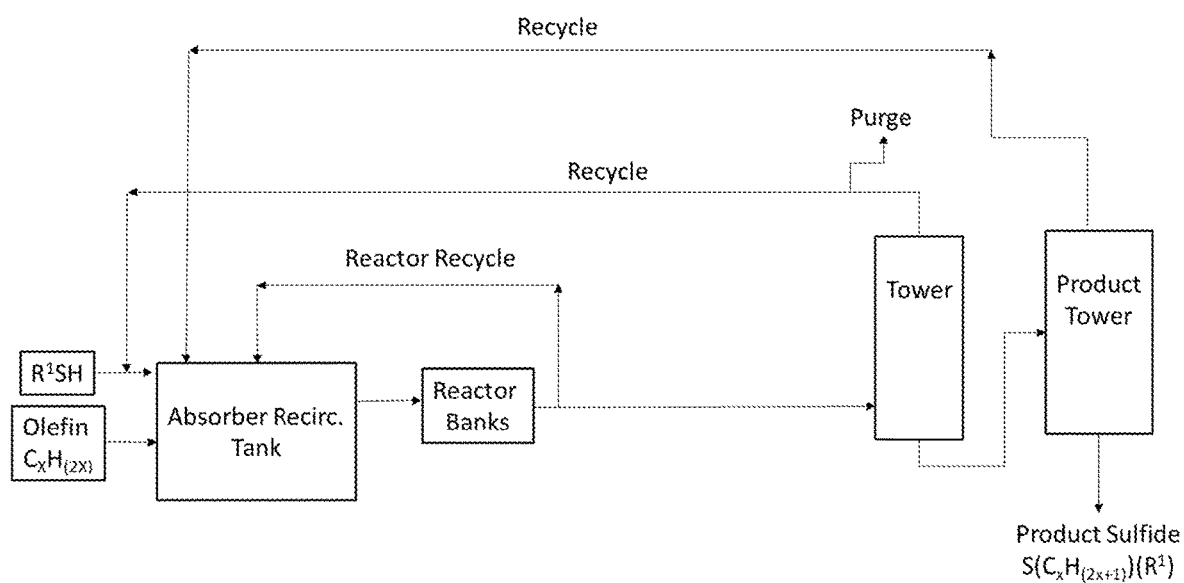

In this embodiment shown in FIG. 5, the reactor is configured to form a reactor effluent stream comprising the product sulfide $[S(C_xH_{(2x+1)})_2$ or $S(C_xH_{(2x+1)})(R^1)]$, unreacted hydrogen sulfide or unreacted $R^1SH$, unreacted olefin of formula $C_xH_{(2x)}$, and other components. These other components may include unreacted thiol $R^1SH$ or unreacted hydrogen sulfide, and other components produced as side reactions in the reactor, and/or other impurities such as heavier or lighter components contained as impurities in the feed stream.

As shown in FIG. 5, a first portion of this reactor effluent stream is recycled back to the reactor system and in the embodiment shown in FIG. 5 is recycled back to the reactor circulating tank that is in communication with the absorber. A second portion of the reactor effluent stream is fed to a sulfide separation system. The sulfide separation system is configured to produce at least one recycle stream including at least a portion of the unreacted hydrogen sulfide or unreacted $R^1SH$, the unreacted olefin of formula $C_xH_{(2x)}$, and other components. The sulfide separation system also produces the product stream comprising the high purity product sulfide, $[S(C_xH_{(2x+1)})_2$ or a $S(C_xH_{(2x+1)})(R^1)]$. As shown in FIG. 5 the sulfide separation system includes two separation units which may be distillation columns called "towers" in FIG. 5. The first separation unit is a distillation column, "tower" configured to receive into the bottom the reactor effluent stream from the reactor system. The first separation unit is also configured to produce as overhead, a recycle stream comprising at least a portion of the unreacted hydrogen sulfide or the unreacted $R^1SH$ depending on which was fed to the reactor system, and other light boiling components. The first separation unit produces from the bottom a crude sulfide stream comprising the product sulfide which is fed to the product sulfide purification system. The product sulfide purification system may be a distillation column and is labelled "product tower" in FIG. 5. The product sulfide purification system distillation column produces as overhead, a second recycle stream comprising at least a portion of the unreacted olefin of formula $C_xH_{(2x)}$ and higher boiling components that were in the first separation unit bottoms, and a sulfide product stream as the bottoms, which comprises the purified product sulfide. As mentioned above, the purified product sulfide is either $S(C_xH_{(2x+1)})_2$ or $S(C_xH_{(2x+1)})(R^1)$, depending on whether hydrogen sulfide or $R^1SH$ is fed to the reactor system with the olefin of formula $C_xH_{(2x)}$. In the embodiment of FIG. 5, $R^1SH$ is fed to the reactor system and accordingly, the product stream is $S(C_xH_{(2x+1)})(R^1)$ sulfide.

Figure 6:
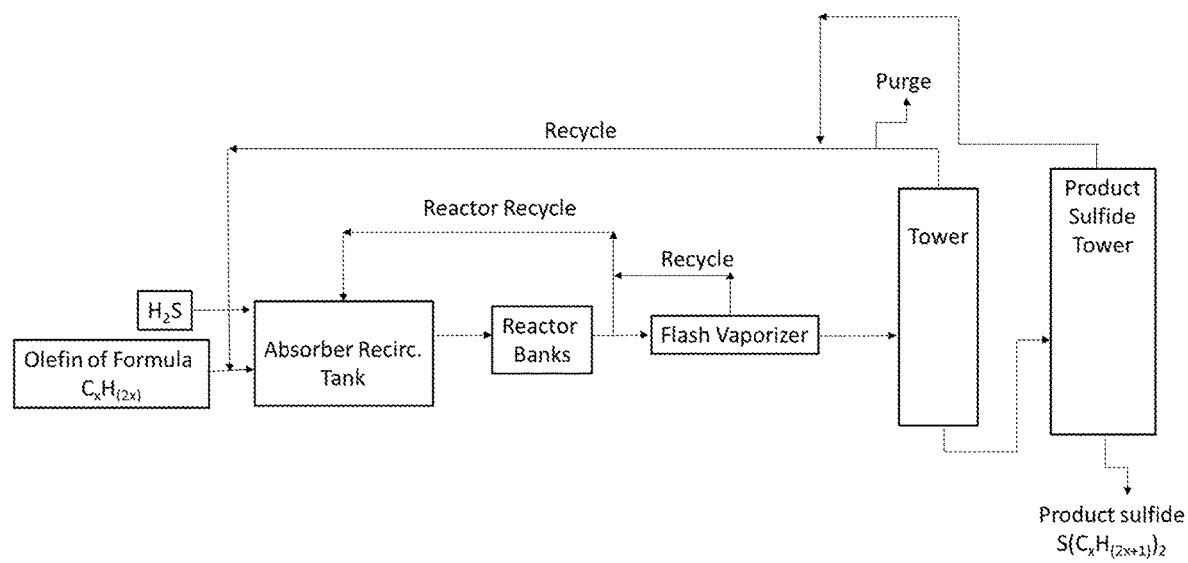
FIG. 6 shows an exemplary process to produce a high purity sulfide according to another embodiment of the invention.

FIG. 6 shows another embodiment of a process to produce sulfide as the desired product. In this exemplary embodiment hydrogen sulfide and olefin of formula $C_xH_{(2x)}$ are fed to the reactor system and accordingly, the desired sulfide product is $S(C_xH_{(2x+1)})_2$. Of course, a person having skill in the art will appreciate that $R^1SH$ may be fed to the reactor system and accordingly, the product stream would be $R^1SR^2$ sulfide, as in FIG. 5. In this exemplary embodiment shown in FIG. 6, a flash vaporizer is in communication with the sulfide separation system and the reactor system. The flash vaporizer is configured to receive the second portion of the reactor effluent, i.e., the portion of the reactor effluent stream that was not immediately recycled back the reactor system. The flash vaporizer is configured to flash off the lights in the reactor effluent stream, by reducing pressure and/or raising the temperature of the portion of the reactor effluent stream, as is known in the art, and thus produces a lights recycle stream that includes at least a portion of the unreacted hydrogen sulfide or unreacted $R^1SH$ or unreacted olefin of formula $C_xH_{(2x)}$, depending on the relative boiling points of the unreacted $R^1SH$ and unreacted olefin of formula $C_xH_{(2x)}$. Also exiting from the flash vaporizer is a crude sulfide stream. In this crude sulfide stream are the heavier (higher boiling) components that were not removed in the flash vaporizer, including the product sulfide, unreacted olefin of formula $C_xH_{(2x)}$ or unreacted $R^1SH$, depending on the relative boiling points of the unreacted $R^1SH$ and unreacted olefin of formula $C_xH_{(2x)}$, and other components (impurities, such as by-products of the reaction, for example). This crude sulfide stream is fed to the sulfide separation system. As shown in FIG. 6, the sulfide separation includes a first separation unit (labelled "tower" in FIG. 6, and which is a distillation column) in communication with the reactor system and a product sulfide purification system in communication with the first separation unit.

The first separation unit is configured to receive the reactor effluent stream from the reactor system. The first separation unit then produces as overhead, a first portion of a recycle stream. This first portion of the recycle stream includes at least a portion of the unreacted hydrogen sulfide or the unreacted $R^1SH$ (depending on which was fed to the reactor system), and other components. The bottoms of the first separation unit is a crude sulfide stream including the product sulfide and the higher boiling components that were fed to the first separation unit and not removed as the overhead in that column. This crude sulfide stream including the product sulfide is fed to the product sulfide purification system. As shown in FIG. 6, the product sulfide purification system is a distillation column (labeled "product sulfide tower"). The product sulfide purification system is configured to produce as overhead, a second portion of the recycle stream. This second portion of the recycle includes the higher boiling components from the first separation unit, that however, are lower boiling than the product sulfide which is removed from the bottom of the product sulfide purification system. As shown in FIG. 6, the product sulfide will be $S(C_xH_{(2x+1)})_2$, since olefin of formula $C_xH_{(2x)}$ and hydrogen sulfide were fed to the reactor system. However, a person having skill in the art will appreciate that this process scheme may be used to produce $S(C_xH_{(2x+1)})(R^1)$ if instead $R^1SH$ and olefin of formula $C_xH_{(2x)}$ are fed to the reactor system.

DETAILED DESCRIPTION

The following description is merely exemplary in nature and is in no way intended to limit the present disclosure or its application or uses.

Synthesis of a linear mercaptan by catalytic addition of hydrogen sulfide to a terminal olefin is represented in equation (1).

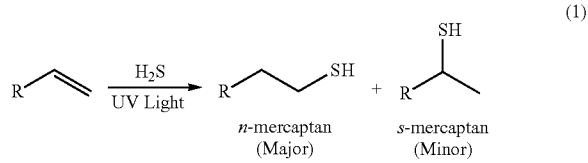

(1)

n-mercaptan (Major)   s-mercaptan (Minor)

An object of this invention is to produce n-dodecyl mercaptan with less than 1000 ppm tetradecylmercaptan and less than 1000 ppm sulfides as impurities on a reproducible basis starting from a 1-dodecene raw material containing up to 2% of 1-tetradecene and other C14 olefins.

In an exemplary embodiment of the present invention, $H_2S$ and a linear alpha olefin (both fresh and from recycle stream) are mixed prior to being fed to the reactor system. This mixture is pumped into reactors in the reactor system and exposed to UV light. The feed flow through the reactor(s) can be varied to pass through a combination of any number of banks or number of tubes, either in series or in parallel, to vary the conversion in the process. The lights in each of the tubes may be independently turned ON or OFF.

Phosphine- or phosphite-based photoinitiators or promoters are preferably not employed in the process as disclosed herein. Non-limiting examples of phosphite compounds that are not included are triarylphosphites, trimethylphosphite, triethylphosphite and tributylphosphite. An important feature of the process for preparing the thiol according to the present invention is that the purified thiol may have less than 15 ppm by weight, such as less than 10 ppm by weight or such as 5 ppm by weight of phosphorus as measured by inductively coupled plasma analysis.

According to some exemplary embodiments, the yield of the thiol production may be adjusted by changing the amount of reactor effluent that is recycled back to the reactor. In a particular embodiment, the reactor recycle amount may be adjusted to maintain the overall weight of the product thiol (e.g., n-octyl mercaptan or n-dodecyl mercaptan) present in the reactor loop to between 30-40 weight percent. Decreasing the concentration of the product thiol affects the overall selectivity of the continuous process as it lowers the amount of unwanted sulfide by-products generated in the process via equation (2).

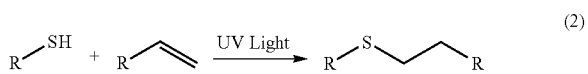

(2)

Increasing conversion by other means when producing the desired thiols, such as by increasing reactor temperature or residence time subjected to the UV light, can undesirably lead to an increase in unwanted sulfides production in the reactor.

Another object of this invention is to make use of the reactor recycle stream to limit the effluent going into the distillation train so as to not overload the downstream rectification (separation) equipment. A further object is to maintain a high $H_2S$/alpha olefin ratio (i.e., higher than 3:1 molar 5:1, 7:1, 10:1 and up to 20:1) in the reaction zone using the reactor recycle stream without having to recompress large quantities of $H_2S$. In a particular embodiment, single-pass olefin conversion through the reactor system is maintained at approximately 40-50% to limit the formation of sulfide by-products inside the reactor. According to some embodiments, the majority (80-90%) of the reactor effluent is recycled back to the absorber recirculation tank via the reactor recycle stream. The recycle line at the outlet of the reactor system may allow for about 65% or 70% or 75% or 80% or 85% or 90% or 95% by weight of the reactor effluent to be recycled back to the recirculation tank in communication with the absorber, where is it mixed with fresh and recycled olefin before re-entering the reactor system. Since $H_2S$ is also recycled in a separate stream from the reactor effluent recycle stream, both fresh $H_2S$ and the recycled $H_2S$ are also introduced into the absorber.

In an exemplary embodiment, the absorber has a recirculating tank in communication with it, and according to some embodiments, the fresh reactants and the recycled reactants are introduced into the recirculating tank before being fed to the absorber and then the reactor system. The absorber and recirculating tank are typically maintained at high pressure. The $H_2S$ is absorbed in the liquid phase (which is typically a mixture of mainly olefin and thiol). The recirculating tank collects the reactor recycle liquid, vaporizer recycle gas (and some liquid) and the recycled olefin from the olefin separations unit and recirculates it through the reactor.

An embodiment of the present invention is a process for producing a high purity linear product thiol from hydrogen sulfide and a linear alpha olefin comprising:

feeding the hydrogen sulfide and the olefin to a reactor system, wherein the reactor system is configured to:

form a reactor effluent stream comprising the product thiol, unreacted hydrogen sulfide, unreacted olefin and other components;

recycling a first portion of the reactor effluent stream to the reactor system;

feeding a second portion of the reactor effluent stream to a flash vaporizer, wherein the flash vaporizer is configured to:

produce a hydrogen sulfide recycle stream comprising at least a portion of the unreacted hydrogen sulfide, and a crude thiol stream comprising the product thiol, the unreacted olefin and the other components;

feeding the hydrogen sulfide recycle stream to the reactor system;

feeding the crude thiol stream to a crude thiol separation system, wherein the crude thiol separation system is configured to:

separate at least a portion of the unreacted olefin from the crude thiol stream to:

produce an olefin recycle stream comprising the unreacted olefin, a first by-product stream comprising a first portion of the other components, and a crude thiol product stream comprising the product thiol and a second portion of the other components;

feeding the olefin recycle stream to the reactor system;

feeding the crude thiol product stream to a product thiol purification unit, wherein the product thiol purification unit is configured to:

produce a thiol product stream comprising purified product thiol comprising at least 98.2 weight percent of the product thiol and a second by-product stream comprising residual product thiol the second portion of the other components.

In an embodiment of the process, the linear alpha olefin comprises, consists essentially of, or consists of a C4-C18 linear alpha olefin.

In an embodiment of the process, the alpha olefin comprises, consists essentially of, or consists of a C12 linear alpha olefin.

In an embodiment of the process, the product thiol comprises, consists essentially of, or consists of n-dodecyl mercaptan and less than 1000 ppm weight tetradecyl mercaptan and less than 1000 ppm sulfides.

In an embodiment of the process, an amount of the first portion of the reactor effluent stream recycled to the reactor system maintains an amount of 20% to 70% by weight of the product thiol in the reactor system.

In an embodiment of the process, the crude thiol separation system comprises an olefin separation unit and a secondary separation unit, and wherein the crude thiol stream is fed to the olefin separation unit, wherein the olefin separation unit is configured to:

produce the olefin recycle stream and a secondary stream; and to feed the secondary stream to the secondary separation unit, and wherein the secondary separation unit is configured to:

separate the secondary stream to produce the first by-product stream and the crude thiol product stream.

The secondary stream contains crude product thiol and by-products of the reaction.

In an embodiment of the process, the second by-product stream comprising the second portion of the other components comprises sulfides and wherein the second by-product stream is fed to a sulfide cracking and stripping unit, wherein the sulfide cracking and stripping unit is configured to:

convert the sulfides into olefins and thiols;

produce a third by-product stream comprising the sulfides; and feed the olefins and thiols to the crude thiol separation system.

In an embodiment of the process, the crude thiol separation system comprises an olefin separation unit and a crude thiol separation unit, and wherein:

the crude thiol stream is fed to the crude thiol separation unit, wherein the crude thiol separation unit is configured to:

produce the crude thiol product stream and a olefin stream containing the first by-product; and to feed the olefin stream containing the first by-product to the olefin separation unit; and wherein:

the olefin separation unit is configured to:

separate the olefin stream containing the first by-product to produce the first by-product stream and the olefin recycle stream.

In an embodiment of the process, the reactor system comprises an absorption unit in communication with a reactor bank, and wherein the absorption unit is configured to:

receive the hydrogen sulfide and the olefin, form a liquid reactor bank feed stream comprising at least a portion of the hydrogen sulfide dissolved in the olefin, and feed the liquid reactor bank feed stream into the reactor bank;

and wherein the reactor bank is configured to:

receive the recycled first portion of the reactor effluent stream and the liquid reactor bank feed stream, and form the reactor effluent stream comprising the product thiol, unreacted hydrogen sulfide, unreacted olefin and other components.

The olefin stream may contain by-products of the reaction which may be removed as the first by-product stream from the olefin separation unit.

In an embodiment of the process, the reactor effluent stream comprises from 20% to 60% by weight of the product thiol.

In an embodiment of the process, the reactor effluent stream comprises from 20% to 55% by weight of the product thiol.

In an embodiment of the process, the reactor effluent stream comprises from 20% to 45% by weight of the product thiol.

In an embodiment of the process, the reactor system is further configured to:

form the product thiol from the hydrogen sulfide and the olefin using electromagnetic radiation and the reactor effluent stream comprises less than 5 wt % of a promoter compound based on the weight of the olefin, and/or less than 5 wt % of an initiator compound.

In an embodiment of the process, the electromagnetic radiation wavelength is from 100 nm to 400 nm, such as 100 nm to 400 nm.

In an embodiment of the process, the promotor compound and/or the initiator compound is selected from the group consisting of alkyl and aryl phosphites, phosphines, azobisisobutyronitrile, benzophenones and derivatives thereof, thiobenzophenones, xanthene compounds, alkylboranes, and mixtures thereof.

In an embodiment of the process, the purified product thiol comprises less than 10 ppm of phosphorous. In various embodiments, the amount of phosphorus is less than 9 ppm, such as less than 8 ppm, such as less than 7 ppm, such as less than 6 ppm, such as less than 5 ppm, such as less than 4 ppm, such as less than 3 ppm, such as less than 2 ppm, such as less than 1 ppm, such as between 0 ppm to less than 10 ppm, such as between 1 to 9 ppm, such as between 1 to 7 ppm, such as between 2 to 8 ppm, such as between 4 to 7 ppm, such as between 1 to 5 ppm, such as between 2 to 6 ppm, such as between 1 to 4 ppm, such as between 1 to 3 ppm, such as between 2 to 4 ppm. The amount of phosphorus was determined by Inductively Coupled Plasma (ICP) mass spectrometry. The samples were digested with sulfuric and nitric acid a the Milestone UltraWAVE microwave digester. The digested samples were diluted gravimetrically. A reagent blank was carried along with the samples and the sample results were corrected for the blank. The samples were analyzed for trace metals against a calibration curve using an Agilent 7700x ICP-MS. The instrument did the background correction. Subsequent dilutions may be performed to bring the desired elements into the calibration range.

In an embodiment of the process, the product thiol purification unit includes at least one distillation column containing structured packing.

An embodiment of the present invention is a composition of the purified product thiol produced according to an embodiment of the process for producing a purified thiol disclosed herein.

According to some embodiments of the purified product thiol produced according to an embodiment of the process for producing a purified thiol, the purified product thiol comprises, consists essentially of, or consists of less than 10 ppm of phosphorous. In various embodiments of the composition of the purified product thiol, the amount of phosphorus is less than 9 ppm, such as less than 8 ppm, such as less than 7 ppm, such as less than 6 ppm, such as less than 5 ppm, such as less than 4 ppm, such as less than 3 ppm, such as less than 2 ppm, such as less than 1 ppm, such as between 0 ppm to less than 10 ppm, such as between 1 to 9 ppm, such as between 1 to 7 ppm, such as between 2 to 8 ppm, such as between 4 to 7 ppm, such as between 1 to 5 ppm, such as between 2 to 6 ppm, such as between 1 to 4 ppm, such as between 1 to 3 ppm, such as between 2 to 4 ppm. The amount of phosphorus was determined by Inductively Coupled Plasma (ICP) mass spectrometry. The samples were digested with sulfuric and nitric acid a the Milestone Ultra-WAVE microwave digester. The digested samples were diluted gravimetrically. A reagent blank was carried along with the samples and the sample results were corrected for the blank. The samples were analyzed for trace metals against a calibration curve using an Agilent 7700x ICP-MS. The instrument did the background correction. Subsequent dilutions may be performed to bring the desired elements into the calibration range. According to some embodiments of the composition of the purified product thiol, the product thiol comprises, consists essentially of, or consists of n-dodecyl mercaptan (NDM). According to some embodiments of the purified product thiol, the product thiol comprises, consists essentially of, or consists of n-octyl mercaptan. According to some exemplary embodiments of composition of the purified product thiol, the purified product thiol comprises, consists essentially of, or consists of n-dodecyl mercaptan and less than 1000 ppm weight tetradecyl mercaptan and less than 1000 ppm sulfides.

An embodiment of the present invention is an apparatus for producing a high purity linear product thiol from hydrogen sulfide and a linear alpha olefin comprising:

a reactor system configured to receive the hydrogen sulfide and the linear alpha olefin and to produce a reactor effluent stream comprising the product linear thiol, unreacted hydrogen sulfide, unreacted linear alpha olefin and other components, and wherein the reactor system is further configured to recycle a first portion of the reactor effluent stream back the reactor system;

a flash vaporizer in communication with the reactor system, wherein the flash vaporizer is configured to receive a second portion of the reactor effluent stream and to produce:

a hydrogen sulfide recycle stream comprising at least a portion of the unreacted hydrogen sulfide, and a crude thiol stream comprising the product linear thiol, the unreacted linear alpha olefin and the other components and wherein the flash vaporizer is configured to feed the hydrogen sulfide recycle stream to the reactor system;

a crude thiol separation system in communication with the flash vaporizer and the reactor system, wherein the crude thiol separation system is configured to receive the crude thiol stream, wherein the crude thiol separation system is configured to:

separate at least a portion of the unreacted linear alpha olefin from the crude thiol stream to produce an olefin recycle stream comprising the unreacted linear alpha olefin, a first by-product stream comprising a first portion of the other components, and a crude thiol product stream comprising the product linear thiol and a second portion of the other components; and feed the olefin recycle stream to the reactor system;

a product thiol purification unit in communication with the crude thiol separation system, wherein the product thiol purification unit is configured to:

receive the crude thiol product stream;

produce a product thiol stream comprising purified product thiol comprising at least 90 weight percent of the product linear thiol and a second by-product stream comprising the second portion of the other components. In an embodiment of the apparatus for producing the purified thiol composition, the purified product thiol stream may comprise at least 95 weight percent of the product thiol, at least 96 weight percent, at least 97 weight percent, at least 98 weight percent, at least 98.5 weight percent, at least 99.0 weight percent, at least 99.5 weight percent of the product thiol.

In an embodiment of the apparatus, the crude thiol separation system comprises an olefin separation unit in communication with a secondary separation unit, and wherein:

the olefin separation unit is in communication with the flash vaporizer and is configured to:

receive the crude thiol stream;

produce the olefin recycle stream and a secondary stream;

feed the secondary stream to the secondary separation unit; and wherein the secondary separation unit is in communication with the product thiol purification unit and is configured to:

receive the secondary stream; and separate the secondary stream to produce the first by-product stream and the crude thiol product stream.

In an embodiment of the apparatus the thiol product purification unit is in communication with the crude thiol separation unit and is configured to:

receive the crude product thiol from the secondary separation unit;

produce a pure product thiol and a second by-product stream containing some residual product thiol.

In an embodiment of the apparatus, the apparatus further comprises a sulfide cracking and stripping unit in communication with the thiol product purification unit and the crude thiol separation unit, wherein the sulfide cracking and stripping unit is configured to:

receive the second by-product stream comprising the second portion of the other components comprising sulfides;

convert at least a portion of the sulfides into olefins and thiols;

produce a third by-product stream comprising unconverted sulfides; and feed the olefins and unconverted thiols to the crude thiol separation unit.

The conversion of sulfides to olefins and thiols may include cracking.

In an embodiment of the apparatus, the crude thiol separation system comprises an olefin separation unit in communication with a crude thiol separation unit, and wherein the crude thiol separation unit is in communication with the flash vaporizer and the product thiol purification unit, and wherein:

the crude thiol separation unit is configured to:
receive the crude thiol stream;
produce the crude product thiol stream and an olefin stream containing the first by-product; and
feed the olefin stream containing the first by-product to the olefin separation unit; and the olefin separation unit is configured to:
separate the olefin stream containing the first by-product;
produce the first by-product stream and the olefin recycle stream.

In an embodiment of the apparatus, the reactor system comprises an absorption unit in communication with a reactor bank, and wherein the absorption unit is configured to:

receive the hydrogen sulfide and the linear alpha olefin,
form a liquid reactor bank feed stream comprising at least a portion of the hydrogen sulfide dissolved in the linear alpha olefin, and
feed the liquid reactor bank feed stream into the reactor bank;
and wherein the reactor bank is configured to:
receive the recycled first portion of the reactor effluent stream and the liquid reactor bank feed stream, and
form the reactor effluent stream comprising the product thiol, unreacted hydrogen sulfide, unreacted linear alpha olefin and other components.

In an embodiment of the apparatus, the product purification unit includes at least one distillation column containing structured packing.

An embodiment of the present invention is a process for producing a high purity product sulfide from hydrogen sulfide or a thiol of formula $R^1$—SH, and an alpha olefin of formula $C_xH_{(2x)}$ comprising:

feeding the hydrogen sulfide or the thiol, and the alpha olefin to a reactor system, wherein the reactor system is configured to:
form a reactor effluent stream comprising the product sulfide, unreacted hydrogen sulfide or unreacted alpha olefin, unreacted linear thiol, and other components;
recycling a first portion of the reactor effluent stream to the reactor system;
feeding a second portion of the reactor effluent stream to a sulfide separation system, wherein the sulfide separation system is configured to:
produce at least one recycle stream comprising at least a portion of the unreacted hydrogen sulfide, the unreacted alpha olefin, the unreacted linear thiol, and other components, and a product stream comprising the high purity product sulfide.

In various embodiments, the thiol is a linear thiol and/or the alpha olefin is a linear alpha olefin.

In an embodiment of the sulfide process, the sulfide separation system comprises a first separation unit in communication with the reactor system and a product sulfide purification system in communication with the first separation unit, and wherein:

the first separation unit is configured to:
receive the reactor effluent stream from the reactor system;
produce a first portion of the at least one recycle stream comprising the at least a portion of the unreacted hydrogen sulfide, the unreacted thiol, and the other components, and a crude sulfide stream comprising the product sulfide; and feed the crude sulfide stream comprising the product sulfide to the product sulfide purification system, wherein the product sulfide purification system is configured to:
produce a second portion of the at least one recycle stream comprising at least a portion of the unreacted alpha olefin, and a sulfide product stream comprising the purified product sulfide.

In an embodiment of the sulfide process, the process comprises a flash vaporizer in communication with the reactor system and the sulfide separation system, and wherein the flash vaporizer is configured to:
receive the second portion of the reactor effluent;
produce a lights recycle stream comprising at least a portion of the unreacted hydrogen sulfide or unreacted thiol or unreacted alpha olefin, and a crude sulfide stream comprising the product sulfide, unreacted alpha olefin or unreacted thiol, and the other components; and
feed the crude sulfide stream to the sulfide separation system.

In an embodiment of the sulfide process, the hydrogen sulfide is fed to the reactor system and the high purity sulfide is of formula $S(C_xH_{(2x+1)})_2$.

In an embodiment of the sulfide process, the linear thiol is fed to the reactor system and the high purity sulfide is one or more of formula $S(C_xH_{(2x+1)})_2$, $S(R^1)_2$ and $S(C_xH_{(2x+1)})(R^1)$.

In an embodiment of the sulfide process, $R^1$ of the $R^1$—SH thiol is methyl, ethyl, propyl, isopropyl, n-butyl, sec. butyl, t-butyl, n-pentyl, isopentyl, n-hexyl, 2-methyl pentyl, other branched hexyl, n-octyl, sec. octyl, 2-ethyl hexyl, n-nonyl, branched nonyl, n-decyl, branched decyl, n-undecyl, branched undecyl, n-dodecyl, branched dodecyl, n-tridecyl, branched tridecyl, n-tetradecyl, branched tetradecyl, n-pentadecyl, branched pentadecyl, n-hexyldecyl, branched hexyldecyl, n-heptadecyl, branched heptadecyl, n-octadecyl, or branched octadecyl. In an embodiment of the sulfide process, the $R^1$ of the thiol may comprise a carboxyl functional group, a carboxylate functional group, an amide functional group or an epoxide functional group.

In an embodiment of the sulfide process, the value of x in the alpha olefin of formula $C_xH_{(2x)}$ is 2-18. The olefin is an alpha olefin but not necessarily linear, for example 2-ethyl hexene-1, 2-butyl octene-1, 2-ethyl decene-1 or a class called vinylidene olefins. In an embodiment of the sulfide process, the alpha olefin may comprise a carboxyl functional group, a carboxylate functional group, an amide functional group or an epoxide functional group. In an embodiment of the sulfide process, the carboxyl, carboxylate and amide functional groups are preferably not conjugated with the double bond of the alpha olefin, An embodiment of the present invention is an apparatus for producing a high purity product sulfide from hydrogen sulfide or a thiol of formula $R^1$—SH, and an alpha olefin of formula $C_xH_{(2x)}$ comprising:

a reactor system, wherein the reactor system is configured to:
receive the hydrogen sulfide or the linear thiol, and the alpha olefin to
form a reactor effluent stream comprising the product sulfide, unreacted hydrogen sulfide or unreacted alpha olefin, unreacted thiol, and other components;
recycle a first portion of the reactor effluent stream to the reactor system;
a sulfide separation system, wherein the sulfide separation system is in communication with the reactor system and is configured to:

receive a second portion of the reactor effluent stream from the reactor system;

produce at least one recycle stream comprising at least a portion of the unreacted hydrogen sulfide, the unreacted alpha olefin, the unreacted thiol, and other components, and a product stream comprising the high purity product sulfide. The apparatus may be configured to produce a high purity linear sulfide from hydrogen sulfide or a linear thiol, together with a linear alpha olefin.

In an embodiment of the sulfide apparatus, the sulfide separation system comprises a first separation unit in communication with the reactor system and a product sulfide purification system in communication with the first separation unit, and wherein the first separation unit is configured to:

receive the reactor effluent stream from the reactor system;

produce a first portion of the at least one recycle stream comprising the at least a portion of the unreacted hydrogen sulfide, the unreacted thiol or the unreacted alpha olefin, and the other components, and a crude sulfide stream comprising the product sulfide; and feed the crude sulfide stream comprising the product sulfide to the product sulfide purification system;

and wherein the product sulfide purification system is configured to:

produce a second portion of the at least one recycle stream comprising at least a portion of the unreacted alpha olefin or the unreacted thiol, and a sulfide product stream comprising the purified product sulfide.

In an embodiment of the sulfide apparatus, the apparatus comprises a flash vaporizer in communication with the reactor system and the sulfide separation system, and wherein the flash vaporizer is configured to:

receive the second portion of the reactor effluent;

produce a lights recycle stream comprising at least a portion of the unreacted hydrogen sulfide or unreacted thiol; or unreacted alpha olefin, and a crude sulfide stream comprising the product sulfide, unreacted alpha olefin or unreacted thiol, and the other components; and feed the crude sulfide stream to the sulfide separation system.

In various embodiments, the high purity linear product thiol is isolated with a purity (wt %) of least 98.2%, such as at least 98.4%, such as at least 98.6%, such as at least 98.8%, such as at least 99.0%, such as at least 99.2%, such as at least 99.4%, such as at least 99.6%, such as at least 99.8%, such as 98.2% to 99.8%, such as 98.2% to 99.6%, such as 98.2% to 99.4%, such as 98.2% to 99.2%, such as 98.4% to 99.6%, such as 98.4% to 99.2%, such as 98.6% to 99.6%, such as 98.8% to 99.6%, such as 99.0% to 99.6%. For example, the thiol purity in weight % may be higher than 90%, preferably higher than 95% and most preferably higher than 98%. The purity may be higher than 91%, higher than 92%, higher than 93%, higher than 94%, higher than 95%, higher than 96%, higher than 96%, or higher than 98%.

In various embodiments, the high purity linear product thiol (also referred to as "mercaptan") is n-octyl mercaptan, n-nonyl mercaptan, n-decyl mercaptan, n-undecyl mercaptan, n-dodecyl mercaptan, n-tridecyl mercaptan, n-tetradecyl mercaptan, n-pentadecyl mercaptan, n-hexyldecyl mercaptan, n-heptadecyl mercaptan or n-octadecyl mercaptan.

In various embodiments, the linear alpha olefin is 1-octene, 1-nonene, 1-decene, 1-undecene, 1-dodecene, 1-tridecene, 1-tetradecene, 1-pentadecene, 1-hexadecene, 1-heptadecene or 1-octadecene.

In various embodiments, the amount of the tetradecyl mercaptan impurity is less than 1000 ppm, such as less than 800 ppm, such as less than 600 ppm, such as less than 400 ppm, such as less than 200 ppm, such as less than 100 ppm, such as less than 80 ppm, such as less than 50 ppm, such as less than 1000 ppm but greater than 50 ppm, such as less than 500 ppm but greater than 50 ppm, such as less than 200 ppm but greater than 50 ppm.

In various embodiments, the amount of the sulfides impurity is less than 1000 ppm, such as less than 800 ppm, such as less than 600 ppm, such as less than 400 ppm, such as less than 200 ppm, such as less than 100 ppm, such as less than 80 ppm, such as less than 50 ppm, such as less than 1000 ppm but greater than 50 ppm, such as less than 500 ppm but greater than 50 ppm, such as less than 200 ppm but greater than 50 ppm.

In various embodiments, the sulfides impurity is n-octyl sulfide, n-nonyl sulfide, n-decyl sulfide, n-undecyl sulfide, n-dodecyl sulfide, n-tridecyl sulfide, n-tetradecyl sulfide, n-pentadecyl sulfide, n-hexyldecyl sulfide, n-heptadecyl sulfide or n-octadecyl sulfide. In some embodiments, the s sulfide impurities may be any of several sulfides made from secondary mercaptans produced as a by-product of the reaction in the process, such as 2-alkyl mercaptans produced from the vinylidene olefins in the feed alpha olefin, for example.

In various embodiments, the amount of linear product thiol present in the first portion of the reactor effluent stream is 20 to 70 wt %, such as 20 to 60 wt %, such as 20 to 55 wt %, such as 20 to 45 wt %, such as 20 to 40 wt %.

In various embodiments, the promoter compound is present an amount of less than 5% based on the weight of the linear alpha olefin or the alpha olefin, such as less than 3%, such as less than 1%. In a particular embodiment, there is no promoter compound present in the process of the present invention as described herein.

In various embodiments, the electromagnetic radiation is ultraviolet radiation, where the source of the radiation is not particularly limited and may include conventional sources such as a mercury arc lamp and light-emitting diodes producing ultraviolet radiation. In addition, the source may be disposed in the reactor or outside the reactor, wherein when the source is disposed outside the reactor, the reactor is transparent in whole or in part and may be formed of Pyrex, Vycor, quartz or other suitable materials.

In various embodiments, the electromagnetic radiation wavelength is from 10 to 600 nm, such as 50 to 600 nm, such as 50 to 400 nm, such as 100 to 400 nm, such as 10 to 300 nm, such as 50 to 300 nm, such as 100 to 300 nm.

In various embodiments, the molar ratio of the $H_2S$ to the linear alpha olefin starting materials is from 20:1 to 3:1, such as 10:1. such as 7:1, such as 5:1, such as 4:1, such as 3:1.

In various embodiments, the reactor system operates at a temperature range of −10 to 120° C. and at a pressure range of 10 to 1,000 psig. In various embodiments, the temperature ranges from −10 to 100° C., such as from −10 to 80° C., such as from −5 to 60° C., such as from 0 to 100° C., such as from 0 to 80° C., such as from 0 to 60° C., such as from 10 to 100° C., such as from 10 to 80° C., such as from 10 to 60° C., such as from 20 to 100° C., such as from 20 to 80° C., such as from 20 to 60° C., such as from 30 to 100° C., such as from 30 to 80° C., such as from 30 to 60° C. In various embodiments, the pressure ranges from 10 to 800 psig, such as from 10 to 600 psig, such as from 10 to 400 psig, such as from 50 to 800 psig, such as from 50 to 600 psig, such as from 50 to 400 psig, such as from 100 to 800 psig, such as from 100 to 600 psig, such as from 100 to 400 psig, such as from 200 to 1,000 psig, such as from 200 to 800 psig, such as from 200 to 600 psig, such as from 200 to 500 psig, such as from 300 to 800 psig, such as from 300 to 600 psig, such as from 400 to 800 psig, such as from 500 to 800 psig.

In various embodiments, the crude thiol separation unit operates at a temperature range of 50 to 260° C. and at a pressure range of −14.7 to 0. psig.

In various embodiments, the thiol purification unit operates at a temperature range of 0 to 500° C. and at a pressure range of −14.7 to 100 psig. In various embodiments, the temperature ranges from 0 to 400° C., such as from 0 to 300° C., such as from 0 to 200° C., such as from 50 to 400° C., such as from 50 to 300° C., such as from 50 to 200° C., such as from 75 to 400° C., such as from 75 to 300° C., such as from 75 to 200° C., such as from 100 to 400° C., such as from 100 to 300° C. In various embodiments, the pressure ranges from −14.7 to 15 psig, such as from −14.7 to 10 psig, such as from −14.7 to 0 psig, such as −14.7 to −10 psig, such as from −14.7 to 15 psig, such as from −14.7 to 10 psig, such as from −14.7 to 0 psig, such as −14.7 to 10 psig, such as from −10 to 15 psig, such as from −10 to 10 psig, such as from −10 to 0 psig, such as from 0 to 15 psig, such as from 0 to 10 psig.

In various embodiments, the olefin separation unit operates at a temperature range of 0 to 500° C. and at a pressure range of −50 to 15 psig. In various embodiments, the temperature ranges from 0 to 400° C., such as from 0 to 300° C., such as from 0 to 200° C., such as from 50 to 400° C., such as from 50 to 300° C., such as from 50 to 200° C., such as from 75 to 400° C., such as from 75 to 300° C., such as from 75 to 200° C., such as from 100 to 400° C., such as from 100 to 300° C. In various embodiments, the pressure ranges from −14.7 to 15 psig, such as from −14.7 to 10 psig, such as from −14.7 to 0 psig, such as −14.7 to −10 psig, such as from −14.7 to 15 psig, such as from −14.7 to 10 psig, such as from −14.7 to 0 psig, such as −14.7 to −10 psig, such as from −10 to 15 psig, such as from −10 to 10 psig, such as from −10 to 0 psig, such as −10 to 10 psig, such as from 0 to 15 psig, such as from 0 to 10 psig.

In various embodiments, the secondary separation unit operates at a temperature range of 0 to 500° C. and at a pressure range of −14.7 to 15 psig. In various embodiments, the temperature ranges from 0 to 400° C., such as from 0 to 300° C., such as from 0 to 200° C., such as from 50 to 400° C., such as from 50 to 300° C., such as from 50 to 200° C., such as from 75 to 400° C., such as from 75 to 300° C., such as from 75 to 200° C., such as from 100 to 400° C., such as from 100 to 300° C. In various embodiments, the pressure ranges from −14.7 to 15 psig, such as from −14.7 to 10 psig, such as from −14.7 to 0 psig, such as −14.7 to −10 psig, such as from −14.7 to 15 psig, such as from −14.7 to 10 psig, such as from −14.7 to 0 psig, such as −14.7 to −10 psig, such as from −10 to 15 psig, such as from −10 to 10 psig, such as from −10 to 0 psig, such as −10 to −10 psig, such as from 0 to 15 psig, such as from 0 to 10 psig.

In various embodiments, the sulfide cracking and stripping unit operates at a temperature range of 50 to 500° C. and at a pressure range of −50 to 15 psig. In various embodiments, the temperature ranges from 50 to 400° C., such as from 50 to 300° C., such as from 50 to 200° C., such as from 100 to 400° C., such as from 100 to 300° C., such as from 150 to 400° C., such as from 150 to 300° C., such as from 200 to 500° C., such as from 200 to 400° C., such as from 300 to 500° C. In various embodiments, the pressure ranges from −14.7 to 15 psig, such as from −14.7 to 10 psig, such as from −14.7 to 0 psig, such as −14.7 to −10 psig, such as from −14.7 to 15 psig, such as from −14.7 to 10 psig, such as from −14.7 to 0 psig, such as −14.7 to −10 psig, such as from −10 to 15 psig, such as from −10 to 10 psig, such as from −10 to 0 psig, such as −10 to −10 psig, such as from 0 to 15 psig, such as from 0 to 10 psig.

In various embodiments, one or more of the thiol separation unit, the thiol purification unit, the olefin separation unit and the secondary separation unit contains at least one distillation column containing structured packing. Suitable packing material includes, but is not limited to, metal packing (e.g., grid packing, plate packing, gauze packing), ceramic packing and plastic packing). Exemplary distillation columns include, but are not limited to, continuous, batch, and HiGee (rotating packed bed) columns.

In various embodiments, the fluid stream of the hydrogen sulfide and the linear alpha olefin reactant fed to the reactor system contains one or more organic solvents such as, but not limited to, hydrocarbon solvents, aromatic solvents, ketone solvents, alcohol solvents, ether solvents, or combinations thereof. Saturated hydrocarbons and those solvents that do not absorb UV light in the above specified range of wavelength or interfere with the reaction are suitable.

Exemplary aspects of the present invention may be summarized as follows:

Aspect 1: A process for producing a high purity product thiol from hydrogen sulfide and an olefin comprising:
feeding the hydrogen sulfide and the olefin to a reactor system, wherein the reactor system is configured to:
  form a reactor effluent stream comprising the product thiol, unreacted hydrogen sulfide, unreacted olefin and other components;
recycling a first portion of the reactor effluent stream to the reactor system;
feeding a second portion of the reactor effluent stream to a flash vaporizer, wherein the flash vaporizer is configured to:
  produce a hydrogen sulfide recycle stream comprising at least a portion of the unreacted hydrogen sulfide, and a crude thiol stream comprising the product thiol, the unreacted olefin and the other components;
feeding the hydrogen sulfide recycle stream to the reactor system;
feeding the crude thiol stream to a crude thiol separation system, wherein the crude thiol separation system is configured to:
  separate at least a portion of the unreacted olefin from the crude thiol stream to:
  produce an olefin recycle stream comprising the unreacted olefin, a first by-product stream comprising a first portion of the other components, and a crude thiol product stream comprising the product thiol and a second portion of the other components;
feeding the olefin recycle stream to the reactor system;
feeding the crude thiol product stream to a product thiol purification unit, wherein the product thiol purification unit is configured to:
  produce a thiol product stream comprising purified product thiol comprising at least 90 weight percent of the product thiol and a second by-product stream comprising the second portion of the other components.

Aspect 2: The process according to claim 1, wherein the olefin comprises a C4-C18 linear alpha olefinic straight-chain hydrocarbon.

Aspect 3: The process according to either claim 1 or claim 2, wherein the olefin comprises C12 linear alpha olefinic straight-chain hydrocarbon, the product thiol comprises n-dodecylmercaptan, and less than 1000 ppm weight tetradecylmercaptan and less than 1000 ppm sulfides.

Aspect 4: The process according to any of claims 1-3, wherein an amount of the first portion of the reactor effluent stream recycled to the reactor system maintains an amount of 20% to 60% by weight of the product thiol in the reactor system.

Aspect 5: The process according to any of claims 1-4,
wherein the crude thiol separation system comprises an olefin separation unit and a secondary separation unit, and
wherein the crude thiol stream is fed to the olefin separation unit,
wherein the olefin separation unit is configured to:
produce the olefin recycle stream and a secondary stream; and to
feed the secondary stream to the secondary separation unit, and
wherein the secondary separation unit is configured to:
separate the secondary stream to produce the first by-product stream and the crude thiol product stream.

Aspect 6: The process according to any of claims 1-5, wherein the second by-product stream comprising the second portion of the other components comprises sulfides and wherein the second by-product stream is fed to a sulfide cracking and stripping unit, wherein the sulfide cracking and stripping unit is configured to:
convert the sulfides into olefins and thiols;
produce a third by-product stream comprising the sulfides; and
feed the olefins and thiols to the crude thiol separation system.

Aspect 7: The process according to any of claims 1-6, wherein the crude thiol separation system comprises an olefin separation unit and a crude thiol separation unit, and wherein: the crude thiol stream is fed to the crude thiol separation unit, wherein the crude thiol separation unit is configured to:
produce the crude thiol product stream and a olefin stream; and to
feed the olefin stream to the olefin separation unit; and
wherein:
the olefin separation unit is configured to:
separate the olefin stream (containing the first-by-product?) to produce the first by-product stream and the olefin recycle stream.

Aspect 8: The process according to any of claims 1-7, wherein the reactor system comprises an absorption unit in communication with a reactor bank, and wherein the absorption unit is configured to:
receive the hydrogen sulfide and the olefin and the recycled first portion of the reactor effluent stream,
form a liquid reactor bank feed stream comprising at least a portion of the hydrogen sulfide dissolved in the olefin and the recycled first portion of the reactor effluent stream, and
feed the liquid reactor bank feed stream into the reactor bank;
and wherein the reactor bank is configured to:
receive the recycled first portion of the reactor effluent stream and the liquid reactor bank feed stream, and
form the reactor effluent stream comprising the product thiol, unreacted hydrogen sulfide, unreacted olefin and other components.

Aspect 9: The process according to any of claims 1-8, wherein the reactor effluent stream comprises from 20% to 70% by weight of the product thiol.

Aspect 10: The process according to any of claims 1-9, wherein the first portion of the reactor effluent stream comprises at least 70 weight percent of a total reactor effluent stream.

Aspect 11: The process according to any of claims 1-10, wherein a conversion of linear alpha olefin to the product thiol in the reactor system is 50 weight percent or less and wherein the amount of sulfide in the reactor is less than 10 weight percent.

Aspect 12: The process according to any of claims 1-11, wherein the reactor system is further configured to: form the product thiol from the hydrogen sulfide and the olefin using electromagnetic radiation, of a wavelength is from 100 nm to 600 nm, and the reactor effluent stream comprises less than 5 weight percent of a promotor compound selected from the group consisting of alkyl boranes, phosphites, azobisisobutyronitrile, benzophenones and derivatives thereof, thiobenzophenones, xanthenic compounds, and mixtures thereof and/or less than 5 weight percent of an initiator compound.

Aspect 13: The process according to any of claims 1-12, wherein the purified product thiol comprises less than 10 ppm weight of phosphorous.

Aspect 14: The process according to any of claims 1-13, wherein the product thiol purification unit includes at least one distillation column containing structured packing.

Aspect 15: An apparatus for producing a high purity product thiol from hydrogen sulfide and an olefin comprising:
a reactor system configured to receive the hydrogen sulfide and the olefin and to produce a reactor effluent stream comprising the product thiol, unreacted hydrogen sulfide, unreacted olefin and other components, and wherein the reactor system is further configured to recycle a first portion of the reactor effluent stream back the reactor system;
a flash vaporizer in communication with the reactor system, wherein the flash vaporizer is configured to receive a second portion of the reactor effluent stream and to produce:
a hydrogen sulfide recycle stream comprising at least a portion of the unreacted hydrogen sulfide, and a crude thiol stream comprising the product thiol, the unreacted olefin and the other components and wherein the flash vaporizer is configured to feed the hydrogen sulfide recycle stream to the reactor system;
a crude thiol separation system in communication with the flash vaporizer and the reactor system, wherein the crude thiol separation system is configured to receive the crude thiol stream, wherein the crude thiol separation system is configured to:
separate at least a portion of the unreacted olefin from the crude thiol stream to produce an olefin recycle stream comprising the unreacted olefin, a first by-product stream comprising a first portion of the other components, and a crude thiol product stream comprising the product thiol and a second portion of the other components; and
feed the olefin recycle stream to the reactor system;
a product thiol purification unit in communication with the crude thiol separation system,
wherein the product thiol purification unit is configured to:
receive the crude thiol product stream;
produce a product thiol stream comprising purified product thiol comprising at least 98.5 weight percent of the product thiol and a second by-product stream comprising the second portion of the other components.

Aspect 16: The apparatus according to claim 15, wherein the crude thiol separation system comprises an olefin separation unit in communication with a secondary separation unit, and wherein:
the olefin separation unit is in communication with the flash vaporizer and is configured to: receive the crude thiol stream;
 produce the olefin recycle stream and a secondary stream;
 feed the secondary stream to the secondary separation unit; and
wherein the secondary separation unit is in communication with the product thiol purification unit and is configured to:
 receive the secondary stream; and
 separate the secondary stream to produce the first by-product stream and the crude thiol product stream.
Aspect 17: The apparatus according to either claim 15 or Aspect 16, further comprising a sulfide cracking and stripping unit in communication with the thiol product purification unit and the crude thiol separation unit, wherein the sulfide cracking and stripping unit is configured to:
 receive the second by-product stream comprising the second portion of the other components comprising sulfides;
 convert the sulfides into olefins and thiols;
 produce a third by-product stream comprising the sulfides; and
 feed the olefins and thiols to the crude thiol separation system.
Aspect 18: The apparatus according to any of claims 15-170, wherein the crude thiol separation system comprises an olefin separation unit in communication with a crude thiol separation unit, and wherein the crude thiol separation unit is in communication with the flash vaporizer and the product thiol purification unit, and wherein:
the crude thiol separation unit is configured to:
 receive the crude stream;
 produce the crude product thiol stream and an olefin stream; and
 feed the olefin stream to the olefin separation unit; and
the olefin separation unit is configured to:
 separate the olefin stream;
 produce the first by-product stream and the olefin recycle stream.
Aspect 19: The apparatus according to any of claims 15-18, wherein the reactor system comprises an absorption unit in communication with a reactor bank, and wherein the absorption unit is configured to:
 receive the hydrogen sulfide and the olefin and the recycled first portion of the reactor effluent stream,
 form a liquid reactor bank feed stream comprising at least a portion of the hydrogen sulfide dissolved in the olefin and the recycled first portion of the reactor effluent stream, and
 feed the liquid reactor bank feed stream into the reactor bank;
and wherein the reactor bank is configured to:
 receive the recycled first portion of the reactor effluent stream and the liquid reactor bank feed stream, and
 form the reactor effluent stream comprising the product thiol, unreacted hydrogen sulfide, unreacted olefin and other components.
Aspect 20: The apparatus according to any of claims 15-19, wherein the product thiol purification unit includes at least one distillation column containing structured packing.
Aspect 21: A process for producing a high purity product sulfide from hydrogen sulfide or $R^1SH$, and an olefin of formula $C_xH_{(2x)}$ comprising:
feeding the hydrogen sulfide or the $R^1SH$, and the olefin of formula $C_xH_{(2x)}$ to a reactor system, wherein the reactor system is configured to:
 form a reactor effluent stream comprising the product sulfide, unreacted hydrogen sulfide or unreacted olefin of formula $C_xH_{(2x)}$, unreacted $R^1SH$, and other components;
recycling a first portion of the reactor effluent stream to the reactor system;
feeding a second portion of the reactor effluent stream to a sulfide separation system, wherein the sulfide separation system is configured to:
 produce at least one recycle stream comprising at least a portion of the unreacted hydrogen sulfide, the unreacted olefin of formula $C_xH_{(2x)}$, the unreacted $R^1SH$, and other components, and a product stream comprising the high purity product sulfide.
Aspect 22: The process according to Aspect 21, wherein the sulfide separation system comprises a first separation unit in communication with the reactor system and a product sulfide purification system in communication with the first separation unit, and wherein:
the first separation unit is configured to:
receive the reactor effluent stream from the reactor system;
produce a first portion of the at least one recycle stream comprising the at least a portion of the unreacted hydrogen sulfide or the unreacted $R^1SH$ or the unreacted olefin of formula $C_xH_{(2x)}$, and the other components, and a crude sulfide stream comprising the product sulfide; and
feed the crude sulfide stream comprising the product sulfide to the product sulfide purification system, wherein the product sulfide purification system is configured to:
produce a second portion of the at least one recycle stream comprising at least a portion of the other of the unreacted olefin of formula $C_xH_{(2x)}$ or the unreacted $R^1SH$, and a sulfide product stream comprising the purified product sulfide.
Aspect 23: The process according to either claim 21 or Aspect 22, comprising a flash vaporizer in communication with the reactor system and the sulfide separation system, and wherein the flash vaporizer is configured to:
receive the second portion of the reactor effluent;
produce a lights recycle stream comprising at least a portion of the unreacted hydrogen sulfide or unreacted $R^1SH$ or unreacted olefin of formula $C_xH_{(2x)}$, and a crude sulfide stream comprising the product sulfide, the other of the unreacted $R^1SH$ or unreacted olefin of formula $C_xH_{(2x)}$, and the other components; and
feed the crude sulfide stream to the sulfide separation system.
Aspect 24: The process according to any of claims 21-23, wherein hydrogen sulfide is fed to the reactor system and the high purity sulfide comprises $S(C_xH_{(2x+1)})_2$.
Aspect 25: The process according to any of claims 21-24, wherein $R^1SH$ is fed to the reactor system and the high purity sulfide comprises $S(C_xH_{(2x+1)})(R^1)$.
Aspect 26: The process according to any of claims 21-25, wherein $R^1$ of the $R^1$—SH thiol is methyl, ethyl, propyl, n-butyl, n-pentyl, n-hexyl, n-octyl, n-nonyl, n-decyl, n-undecyl, n-dodecyl, n-tridecyl, n-tetradecyl, n-pentadecyl, n-hexyldecyl, n-heptadecyl or n-octadecyl.
Aspect 27: The process according to any of claims 21-26, wherein for the olefin of formula $C_xH_{(2x)}$, x is an integer from 2 to 18.
Aspect 28: An apparatus for producing a high purity product sulfide from hydrogen sulfide or $R^1SH$, and an olefin of formula $C_xH_{(2x)}$ comprising:

a reactor system, wherein the reactor system is configured to:
  receive the hydrogen sulfide or the R$^1$SH, and the olefin of formula C$_x$H$_{(2x)}$ to form a reactor effluent stream comprising the product sulfide, unreacted hydrogen sulfide or unreacted olefin of formula C$_x$H$_{(2x)}$, unreacted R$^1$SH, and other components;
  recycle a first portion of the reactor effluent stream to the reactor system;
a sulfide separation system, wherein the sulfide separation system is in communication with the reactor system and is configured to:
  receive a second portion of the reactor effluent stream from the reactor system;
  produce at least one recycle stream comprising at least a portion of the unreacted hydrogen sulfide, the unreacted olefin of formula C$_x$H$_{(2x)}$, the unreacted R$^1$SH, and other components, and a product stream comprising the high purity product sulfide.

Aspect 29: The apparatus according to claim 28, wherein the sulfide separation system comprises a first separation unit in communication with the reactor system and a product sulfide purification system in communication with the first separation unit, and
wherein the first separation unit is configured to:
  receive the reactor effluent stream from the reactor system;
  produce a first portion of the at least one recycle stream comprising the at least a portion of the unreacted hydrogen sulfide, the unreacted R$^1$SH or the unreacted olefin of formula C$_x$H$_{(2x)}$, and the other components, and a crude sulfide stream comprising the product sulfide and the other of the unreacted R$^1$SH or the unreacted olefin of formula C$_x$H$_{(2x)}$; and
  feed the crude sulfide stream comprising the product sulfide to the product sulfide purification system;
and wherein the product sulfide purification system is configured to:
  produce a second portion of the at least one recycle stream comprising at least a portion of the other of the unreacted R$^1$SH or the unreacted olefin of formula C$_x$H$_{(2x)}$, and a sulfide product stream comprising the purified product sulfide.

Aspect 30: The apparatus according to either claim 28 or Aspect 29, comprising a flash vaporizer in communication with the reactor system and the sulfide separation system, and wherein the flash vaporizer is configured to:
  receive the second portion of the reactor effluent;
  produce a lights recycle stream comprising at least a portion of the unreacted hydrogen sulfide or the unreacted R$^1$SH or the unreacted olefin of formula C$_x$H$_{(2x)}$, and a crude sulfide stream comprising the product sulfide, the other of the unreacted R$^1$SH or the unreacted olefin of formula C$_x$H$_{(2x)}$, and the other components; and
  feed the crude sulfide stream to the sulfide separation system.

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the curable compositions, materials, products and articles prepared therefrom and methods for making and using such curable compositions described herein. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

EXAMPLES

Example 1

A 1:10 molar mixture of dodecene-1 and liquid H$_2$S is pumped through the reactor tube until a steady flow is established. Then the UV light is turned on and the mixture is recirculated until the conversion to NDM has reached 20-60%. Then a part of the mixture is fed to a vaporizer that takes all, if not most of the H$_2$S overhead and back to the reactor loop. The liquid is then pushed to the olefin tower where the unreacted olefin is taken overhead and recycled back to the reactor. The olefin tower bottoms are pushed to the secondary tower where the secondary mercaptans and any residual hydrocarbons are taken overhead and the crude product stream is taken from the secondary tower bottoms and pushed to the product tower. Here the product NDM is taken overhead and the sulfides by-product containing residual NDM is taken from the product tower bottoms and pushed to the residue stripper, which strips most if not all the NDM present and partially cracks the sulfide to olefins and NDM that are recycled back to the olefin tower. Product NDM is analyzed by gas chromatography for purity and by mercaptan sulfur titration for the sulfur content and the conditions of the product tower modified to obtain the NDM product purity on specification.

Table 1 below shows how the process of the present invention results in the preparation of high purity mercaptans. For n-dodecyl mercaptan, the levels of the undesired tetradecyl mercaptan and sulfide impurities were significantly below 0.1%.

TABLE 1

Results from Example 1

| Product | n-octyl mercaptan | n-dodecyl mercaptan |
| --- | --- | --- |
| Column Packing Type | Structured Packing | Structured Packing |
| Purity, wt % | 99.48 | 98.82 |
| Tetradecyl mercaptan, wt % | n/a | 0.049 |
| Sulfide, wt % | 0.118 | 0.090 |
| Secondary SH, wt % | 0.349 | 0.880 |
| Olefin, wt % | 0.010 | 0.102 |

Example 2

Hydrogen sulfide at 360 psig and 37° C. and olefin at 360 psig and ambient temperature are introduced in the absorber recirculation tank prior to being passed into the photochemical reactor operating at 40° C. and 450 psig where the catalytic addition of hydrogen sulfide to a terminal olefin occurs via UV light catalysis. The majority (65-90%) of the reactor effluent is recycled back to the absorber recirculation tank via a reactor recycle line. The remainder of the reactor effluent is sent to the flash vaporizer operating at 150° C. and 370 psig. The remaining liquid, essentially free of $H_2S$, is then introduced into the olefin distillation tower (OT) operating at a pressure of 100 mm Hga, a bottoms temperature of 204-230° C., and a reflux ratio of 0.2-0.5. The olefin tower separates the unreacted olefins from the mercaptans and sulfide products. The olefins removed from the top of this tower are sent back to the absorber recirculation tank via the fresh olefin supply line. The effluent from the bottom the olefin tower is introduced to a secondary mercaptan distillation tower operating at a pressure of 50 mmHga, a bottoms temperature of 221-232° C. and a reflux ratio of 15-60. The secondary tower removes the secondary mercaptans produced as a byproduct of the UV catalyzed reaction. The tower bottom effluent of this tower is introduced into a product distillation tower (PT), equipped with structured packing as internals and operating at a pressure of 25 mmHga, a bottoms temperature of 182-232° C., and a reflux ratio of 0.2-1. The final product n-dodecylmercaptan is withdrawn as an overhead product.

Figure 1:
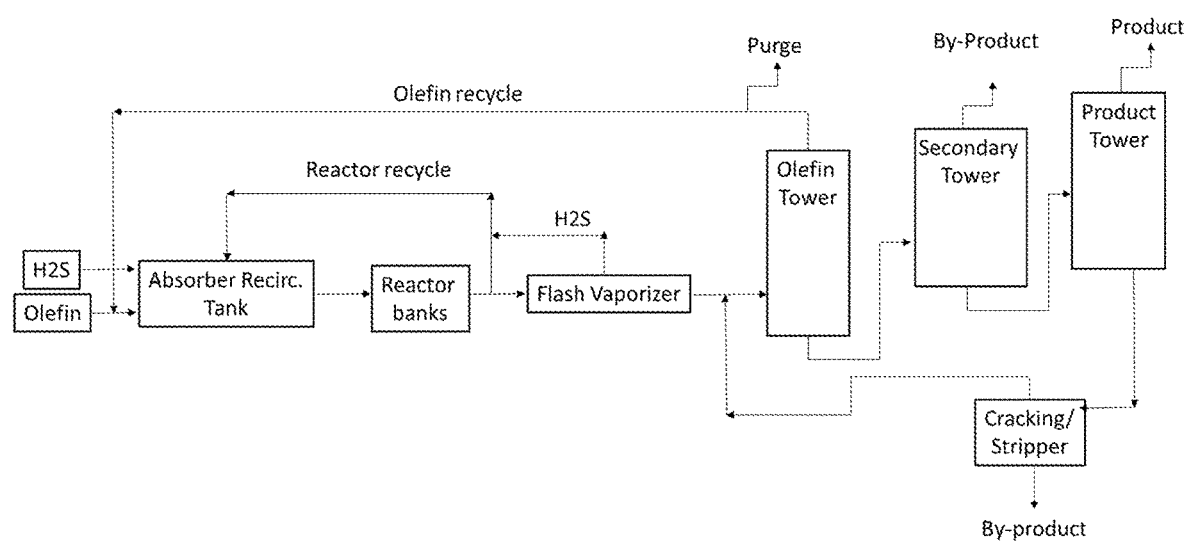
FIG. 1 shows an exemplary process to produce a high purity linear thiol according to an embodiment of the invention.
Figure 2:
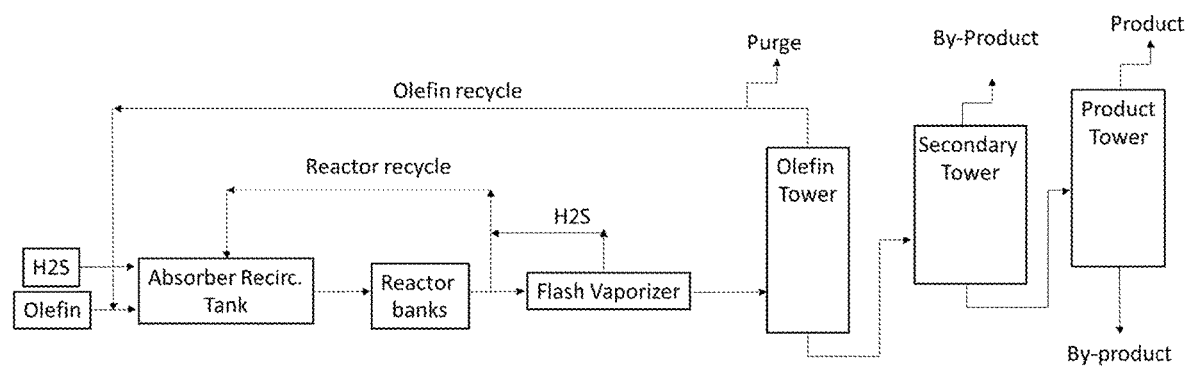
FIG. 2 shows an exemplary process to produce a high purity linear thiol according to another embodiment of the invention
Figure 3:
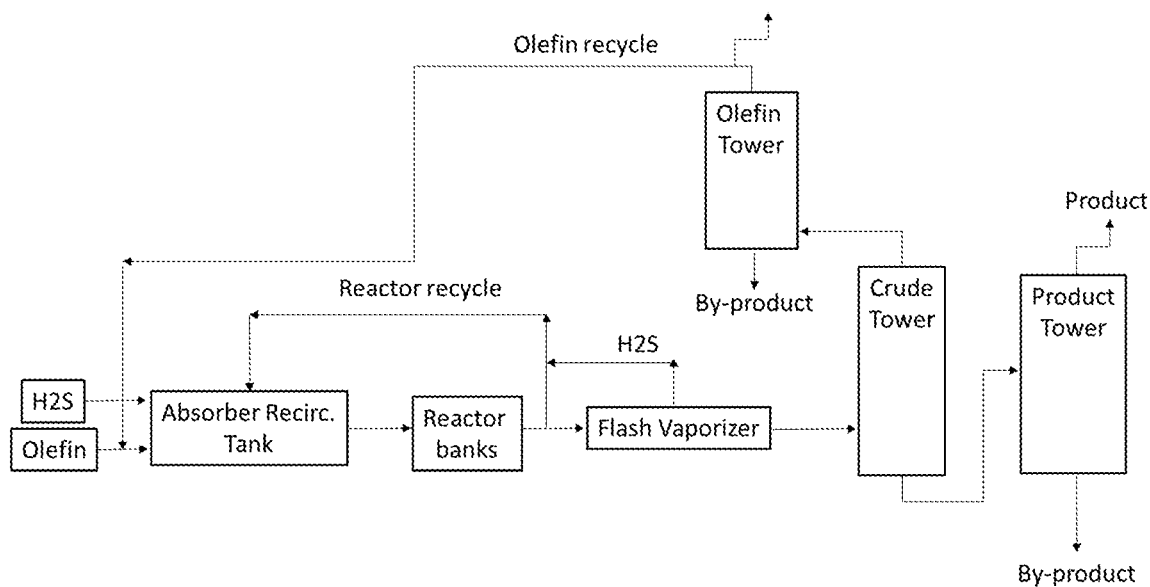
FIG. 3 shows an exemplary process to produce a high purity linear thiol according to still another embodiment of the invention.
Figure 4:
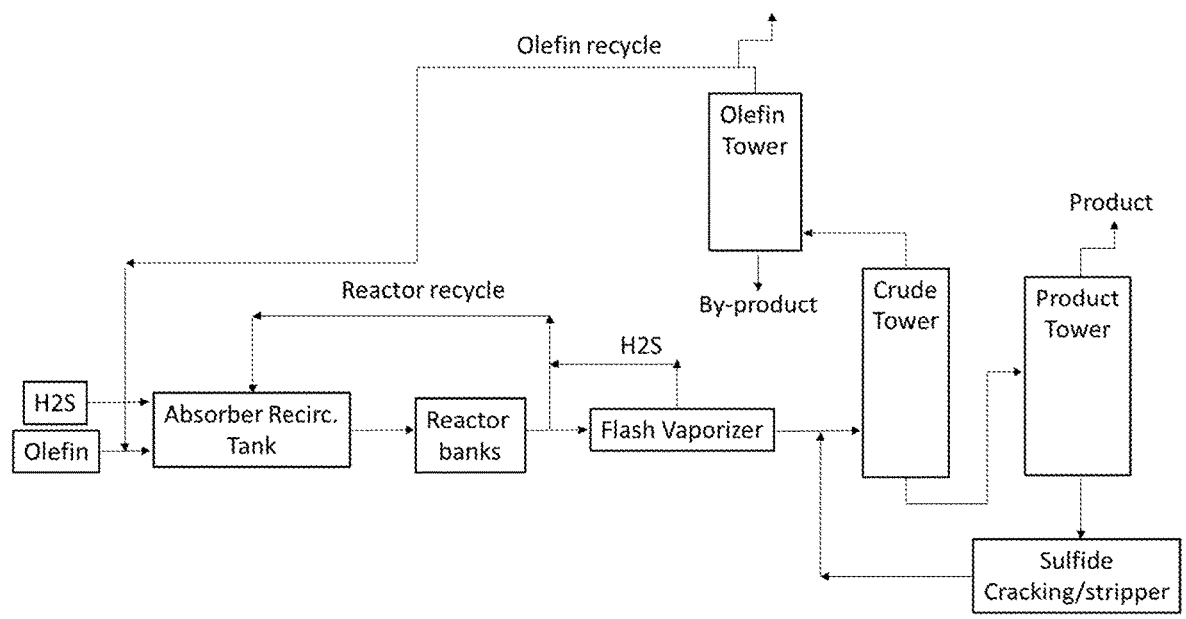
FIG. 4 shows an exemplary process to produce a high purity linear thiol according to yet another embodiment of the invention.

In this example, hydrogen sulfide and 1-dodecene as the olefin were fed to the reactor system shown in FIG. 1 and n-dodecylthiol, also called n-dodecylmercaptan (NDM) was the product thiol. Various streams were analyzed by gas chromatography. The compositions of the streams were monitored by gas chromatography (GC) equipped with a flame ionization detector (FID) and were found to have the compositions as shown in Table 2:

TABLE 2

Example 2 Results

| Stream | NDM, wt % | Olefin, wt % | C14 thiol, wt % | Secondary thiol, wt % | Sulfides, wt % |
|---|---|---|---|---|---|
| Reactor effluent | 35.5 | 59.3 | 0.005 | 2.8 | 2.1 |
| Olefin tower bottoms | 85.6 | 0.9 | 0.3 | 7.6 | 5.5 |
| Olefin tower overhead | 0.5 | 99.3 | 0.0 | 0.2 | 0.0 |
| Secondary tower overhead | 0.6 | 22.7 | 0.0 | 76.6 | 0.1 |
| Purified Product | 98.6 | 0.16 | 0.07 | 1.1 | 0.02 |

What is claimed is:

1. A process for producing a high purity product thiol from hydrogen sulfide and an olefin comprising:
   feeding the hydrogen sulfide and the olefin to a reactor system, wherein the reactor system is configured to:
      form a reactor effluent stream comprising the product thiol, unreacted hydrogen sulfide, unreacted olefin and other components;
      separating said reactor effluent stream into a first portion and a second portion;
      recycling said first portion of the reactor effluent stream to the reactor system;
      feeding said second portion of the reactor effluent stream to a flash vaporizer, wherein the flash vaporizer is configured to:
         produce a hydrogen sulfide recycle stream comprising at least a portion of the unreacted hydrogen sulfide, and a crude thiol stream comprising the product thiol, the unreacted olefin and the other components;
      feeding the hydrogen sulfide recycle stream to the reactor system;
      feeding the crude thiol stream to a crude thiol separation system, wherein the crude thiol separation system is configured to:
         separate at least a portion of the unreacted olefin from the crude thiol stream to:
            produce an olefin recycle stream comprising the unreacted olefin, a first by-product stream comprising a first portion of the other components, and a crude thiol product stream comprising the product thiol and a second portion of the other components;
      feeding the olefin recycle stream to the reactor system;
      feeding the crude thiol product stream to a product thiol purification unit, wherein the product thiol purification unit is configured to:
         produce a thiol product stream comprising purified product thiol comprising at least 90 weight percent of the product thiol and a second by-product stream comprising the second portion of the other components.

2. The process according to claim 1, wherein the olefin comprises a C4-C18 linear alpha olefinic straight-chain hydrocarbon.

3. The process according to claim 1, wherein the olefin comprises C12 linear alpha olefinic straight-chain hydrocarbon, the product thiol comprises n-dodecylmercaptan, and less than 1000 ppm weight tetradecylmercaptan and less than 1000 ppm sulfides.

4. The process according to claim 1, wherein an amount of the first portion of the reactor effluent stream recycled to the reactor system maintains an amount of 20% to 60% by weight of the product thiol in the reactor system.

5. The process according to claim 1,
   wherein the crude thiol separation system comprises an olefin separation unit and a secondary separation unit, and
   wherein the crude thiol stream is fed to the olefin separation unit,
   wherein the olefin separation unit is configured to:
      produce the olefin recycle stream and a secondary stream; and to
      feed the secondary stream to the secondary separation unit, and
   wherein the secondary separation unit is configured to:
      separate the secondary stream to produce the first by-product stream and the crude thiol product stream.

6. The process according to claim 1, wherein the second by-product stream comprising the second portion of the other components comprises sulfides and wherein the second by-product stream is fed to a sulfide cracking and stripping unit, wherein the sulfide cracking and stripping unit is configured to:
   convert the sulfides into olefins and thiols;
   produce a third by-product stream comprising the sulfides; and
   feed the olefins and thiols to the crude thiol separation system.

7. The process according to claim 1, wherein the crude thiol separation system comprises an olefin separation unit and a crude thiol separation unit, and wherein:
   the crude thiol stream is fed to the crude thiol separation unit, wherein the crude thiol separation unit is configured to:
      produce the crude thiol product stream and a olefin stream; and to
      feed the olefin stream to the olefin separation unit; and
   wherein:
   the olefin separation unit is configured to:
      separate the olefin stream to produce the first by-product stream and the olefin recycle stream.

8. The process according to claim 1, wherein the reactor system comprises an absorption unit in communication with a reactor bank, and wherein the absorption unit is configured to:
  receive the hydrogen sulfide and the olefin and the recycled first portion of the reactor effluent stream,
  form a liquid reactor bank feed stream comprising at least a portion of the hydrogen sulfide dissolved in the olefin and the recycled first portion of the reactor effluent stream, and
  feed the liquid reactor bank feed stream into the reactor bank;
and wherein the reactor bank is configured to:
  receive the recycled first portion of the reactor effluent stream and the liquid reactor bank feed stream, and
  form the reactor effluent stream comprising the product thiol, unreacted hydrogen sulfide, unreacted olefin and other components.

9. The process according to claim 1, wherein the reactor effluent stream comprises from 20% to 70% by weight of the product thiol.

10. The process according to claim 1, wherein the first portion of the reactor effluent stream comprises at least 70 weight percent of a total reactor effluent stream.

11. The process according to claim 1, wherein a conversion of linear alpha olefin to the product thiol in the reactor system is 50 weight percent or less and wherein the amount of sulfide in the reactor is less than 10 weight percent.

12. The process according to claim 1, wherein the reactor system is further configured to:
  form the product thiol from the hydrogen sulfide and the olefin using electromagnetic radiation, of a wavelength is from 100 nm to 600 nm, and the reactor effluent stream comprises less than 5 weight percent of a promotor compound selected from the group consisting of alkyl boranes, phosphites, azobisisobutyronitrile, benzophenones and derivatives thereof, thiobenzophenones, xanthenic compounds, and mixtures thereof and/or less than 5 weight percent of an initiator compound.

13. The process according to claim 1, wherein the purified product thiol comprises less than 5 ppm weight of phosphorous.

14. The process according to claim 1, wherein the product thiol purification unit includes at least one distillation column containing structured packing.

15. An apparatus for producing a high purity product thiol from hydrogen sulfide and an olefin comprising:
  a reactor system configured to receive the hydrogen sulfide and the olefin and to produce a reactor effluent stream comprising the product thiol, unreacted hydrogen sulfide, unreacted olefin and other components, and wherein the reactor system is further configured to separate said reactor effluent stream into a first portion and a second portion and recycle said first portion of the reactor effluent stream back to the reactor system;
  a flash vaporizer in communication with the reactor system, wherein the flash vaporizer is configured to receive said second portion of the reactor effluent stream and to produce:
  a hydrogen sulfide recycle stream comprising at least a portion of the unreacted hydrogen sulfide, and a crude thiol stream comprising the product thiol, the unreacted olefin and the other components and wherein the flash vaporizer is configured to feed the hydrogen sulfide recycle stream to the reactor system;
  a crude thiol separation system comprising an olefin separation unit in communication with a secondary separation unit, and wherein:
  the olefin separation unit is in communication with the flash vaporizer and the reactor system, and is configured to:
    receive the crude thiol stream;
    produce an olefin recycle stream and a secondary stream;
    feed the olefin recycle stream to the reactor system;
    feed the secondary stream to the secondary separation unit; and
  wherein the secondary separation unit is in communication with the product thiol purification unit and is configured to:
    receive the secondary stream; and
    separate the secondary stream to produce the first by-product stream and the crude thiol product stream;
  a product thiol purification unit in communication with the crude thiol separation system, wherein the product thiol purification unit is configured to:
    receive the crude thiol product stream;
    produce a product thiol stream comprising purified product thiol comprising at least 98.5 weight percent of the product thiol and a second by-product stream comprising the second portion of the other components.

16. The apparatus according to claim 15, wherein the product thiol purification unit includes at least one distillation column containing structured packing.

17. A process for producing a high purity product sulfide from hydrogen sulfide or $R^1SH$, and an olefin of formula $C_xH_{(2x)}$ comprising:
  feeding the hydrogen sulfide or the $R^1SH$, and the olefin of formula $C_xH_{(2x)}$ to a reactor system, wherein the reactor system is configured to:
    form a reactor effluent stream comprising the product sulfide, unreacted hydrogen sulfide or unreacted olefin of formula $C_xH_{(2x)}$), unreacted $R^1SH$, and other components;
  separating said reactor effluent stream into a first portion and a second portion;
  recycling said first portion of the reactor effluent stream to the reactor system;
  feeding said second portion of the reactor effluent stream to a sulfide separation system, wherein the sulfide separation system is configured to:
    produce at least one recycle stream comprising at least a portion of the unreacted hydrogen sulfide, the unreacted olefin of formula $C_xH_{(2x)}$, the unreacted $R^1SH$, and other components, and a product stream comprising the high purity product sulfide.

18. The process according to claim 17, wherein the sulfide separation system comprises a first separation unit in communication with the reactor system and a product sulfide purification system in communication with the first separation unit, and wherein:
  the first separation unit is configured to:
    receive the reactor effluent stream from the reactor system;
    produce a first portion of the at least one recycle stream comprising the at least a portion of the unreacted hydrogen sulfide or the unreacted $R^1SH$ or the unreacted olefin of formula $C_xH_{(2x)}$, and the other components, and a crude sulfide stream comprising the product sulfide; and feed the crude sulfide stream comprising the product sulfide to the product sulfide purification system, wherein the product sulfide purification system is configured to:
produce a second portion of the at least one recycle stream comprising at least a portion of the other of the unreacted olefin of formula $C_xH_{(2x)}$) or the unreacted $R^1SH$, and a sulfide product stream comprising the purified product sulfide.

19. The process according to claim 17, comprising a flash vaporizer in communication with the reactor system and the sulfide separation system, and wherein the flash vaporizer is configured to:
receive the second portion of the reactor effluent;
produce a lights recycle stream comprising at least a portion of the unreacted hydrogen sulfide or unreacted $R^1SH$ or unreacted olefin of formula $C_xH_{(2x)}$), and a crude sulfide stream comprising the product sulfide, the other of the unreacted $R^1SH$ or unreacted olefin of formula $C_xH_{(2x)}$), and the other components; and
feed the crude sulfide stream to the sulfide separation system.

20. The process according to claim 17, wherein hydrogen sulfide is fed to the reactor system and the high purity sulfide comprises $S(C_xH_{(2x+1)})_2$.

21. The process according to claim 17, wherein $R^1SH$ is fed to the reactor system and the high purity sulfide comprises $S(C_xH_{(2x+1)})(R^1)$.

22. The process according to claim 17, wherein $R^1$ of the $R^1$—SH thiol is methyl, ethyl, propyl, n-butyl, n-pentyl, n-hexyl, n-octyl, n-nonyl, n-decyl, n-undecyl, n-dodecyl, n-tridecyl, n-tetradecyl, n-pentadecyl, n-hexyldecyl, n-heptadecyl or n-octadecyl.

23. The process according to claim 17, wherein for the olefin of formula $C_xH_{(2x)}$, x is an integer from 2 to 18.

24. An apparatus for producing a high purity product thiol from hydrogen sulfide and an olefin comprising:
a reactor system comprising an absorption unit in communication with a reactor bank, wherein the absorption unit is configured to:
receive the hydrogen sulfide and the olefin,
form a liquid reactor bank feed stream comprising at least a portion of the hydrogen sulfide dissolved in the olefin and a recycled first portion of a reactor effluent stream, and feed a liquid reactor bank feed stream into the reactor bank;
and wherein the reactor bank is configured to:
receive the recycled first portion of the reactor effluent stream and the liquid reactor bank feed stream, and
form the reactor effluent stream comprising the product thiol, unreacted hydrogen sulfide, unreacted olefin and other components;
means to to separate said reactor effluent stream into a first portion and a second portion and recycle said first portion of the reactor effluent stream back to the reactor system;
a flash vaporizer in communication with the reactor system, wherein the flash vaporizer is configured to receive said second portion of the reactor effluent stream and to produce:
a hydrogen sulfide recycle stream comprising at least a portion of the unreacted hydrogen sulfide, and a crude thiol stream comprising the product thiol, the unreacted olefin and the other components and wherein the flash vaporizer is configured to feed the hydrogen sulfide recycle stream to the reactor system;
a crude thiol separation system in communication with the flash vaporizer and the reactor system, wherein the crude thiol separation system is configured to receive the crude thiol stream, wherein the crude thiol separation system is configured to:
separate at least a portion of the unreacted olefin from the crude thiol stream to produce an olefin recycle stream comprising the unreacted olefin, a first by-product stream comprising a first portion of the other components, and a crude thiol product stream comprising the product thiol and a second portion of the other components; and
feed the olefin recycle stream to the reactor system;
a product thiol purification unit in communication with the crude thiol separation system, wherein the product thiol purification unit is configured to:
receive the crude thiol product stream;
produce a product thiol stream comprising purified product thiol comprising at least 98.5 weight percent of the product thiol and a second by-product stream comprising the second portion of the other components.

* * * * *